(12) United States Patent
Horn

(10) Patent No.: US 8,445,526 B2
(45) Date of Patent: *May 21, 2013

(54) COMPOSITIONS AND METHODS FOR TREATMENT OF GLAUCOMA

(75) Inventor: Gerald Horn, Deerfield, IL (US)

(73) Assignee: Glaucoma & Nasal Therapies LLC, Dana Point, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/585,563

(22) Filed: Aug. 14, 2012

(65) Prior Publication Data

US 2012/0309804 A1    Dec. 6, 2012

Related U.S. Application Data

(63) Continuation-in-part of application No. 13/365,138, filed on Feb. 2, 2012, now abandoned, which is a continuation-in-part of application No. 12/931,632, filed on Feb. 3, 2011.

(51) Int. Cl.
| | |
|---|---|
| *A01N 43/50* | (2006.01) |
| *A61K 31/415* | (2006.01) |
| *C07D 233/00* | (2006.01) |
| *C07D 233/02* | (2006.01) |
| *C07D 233/56* | (2006.01) |
| *C07D 233/58* | (2006.01) |

(52) U.S. Cl.
USPC .................... 514/396; 548/300.1; 548/335.1; 548/346.1

(58) Field of Classification Search
USPC .................. 514/396; 548/300.1, 335.1, 346.1
See application file for complete search history.

(56) References Cited

U.S. PATENT DOCUMENTS

| | | | |
|---|---|---|---|
| 5,304,569 | A | 4/1994 | Lammintausta et al. |
| 5,424,078 | A | 6/1995 | Dziabo et al. |
| 5,605,911 | A | 2/1997 | Olney et al. |
| 5,712,301 | A | 1/1998 | Heinonen et al. |
| 6,194,415 | B1 | 2/2001 | Wheeler et al. |
| 6,248,741 | B1 | 6/2001 | Wheeler et al. |
| 6,465,464 | B2 | 10/2002 | Wheeler et al. |
| 6,562,855 | B1 | 5/2003 | Franks et al. |
| 6,562,873 | B2 | 5/2003 | Olejnik et al. |
| 6,627,210 | B2 | 9/2003 | Olejnik et al. |
| 6,641,834 | B2 | 11/2003 | Olejnik et al. |
| 6,653,354 | B2 | 11/2003 | Franks et al. |
| 6,673,337 | B2 | 1/2004 | Olejnik et al. |
| 6,916,811 | B2 | 7/2005 | Boyle et al. |
| 7,030,149 | B2 | 4/2006 | Chang et al. |
| 7,309,706 | B2 | 12/2007 | Rupp et al. |
| 7,589,057 | B2 | 9/2009 | Chang et al. |
| 7,678,829 | B2 | 3/2010 | Matier et al. |
| 2001/0018821 | A1 | 9/2001 | Chow et al. |
| 2002/0156076 | A1 | 10/2002 | Chow et al. |
| 2002/0197300 | A1 | 12/2002 | Schultz et al. |
| 2003/0181354 | A1 | 9/2003 | Abdulrazik |
| 2003/0229088 | A1 | 12/2003 | Donello et al. |
| 2004/0132824 | A1 | 7/2004 | Donello et al. |
| 2004/0266776 | A1 | 12/2004 | Gil et al. |
| 2005/0058696 | A1 | 3/2005 | Donello et al. |
| 2005/0059664 | A1 | 3/2005 | Gil et al. |
| 2005/0059744 | A1 | 3/2005 | Donello et al. |
| 2005/0244468 | A1 | 11/2005 | Huang et al. |
| 2005/0244474 | A1 | 11/2005 | Huang et al. |
| 2006/0264442 | A1 | 11/2006 | Ruiz et al. |
| 2007/0031472 | A1 | 2/2007 | Huang et al. |
| 2007/0203085 | A1 | 8/2007 | Lang |
| 2008/0020076 | A1 | 1/2008 | Jhamandas et al. |
| 2008/0131483 | A1 | 6/2008 | Abdulrazik |
| 2008/0131485 | A1 | 6/2008 | Huang et al. |
| 2008/0207627 | A1 | 8/2008 | Gil et al. |
| 2008/0207628 | A1 | 8/2008 | Gil et al. |
| 2009/0176843 | A1 | 7/2009 | Sinha et al. |
| 2009/0220611 | A1 | 9/2009 | Castan et al. |
| 2010/0028266 | A1 | 2/2010 | Horn |
| 2010/0029659 | A1 | 2/2010 | Horn |
| 2010/0029661 | A1 | 2/2010 | Horn |
| 2010/0029662 | A1 | 2/2010 | Horn |
| 2010/0029663 | A1 | 2/2010 | Horn |

FOREIGN PATENT DOCUMENTS

| | | |
|---|---|---|
| WO | 2009022096 A1 | 2/2009 |
| WO | 2009124755 A1 | 4/2009 |
| WO | 2010014552 | 2/2010 |

OTHER PUBLICATIONS

U.S. Appl. No. 13/066,368, filed Apr. 2011, Horn.*
U.S. Appl. No. 13/066,370, filed Apr. 2011, Horn.*
U.S. Appl. No. 12/800,942, filed May 2010, Horn.*
U.S. Appl. No. 13/606,637, filed Sep. 2012, Horn.*
U.S. Appl. No. 13/585,602, filed Aug. 2012, Horn.*
U.S. Appl. No. 13/406,321, filed Feb. 2012, Horn.*
U.S. Appl. No. 12/928,749, filed Feb. 2011, Horn.*
U.S. Appl. No. 12/928,761, filed Feb. 2011, Horn.*
U.S. Appl. No. 12/931,632, filed Feb. 2011, Horn.*
Gilsbach et al., Genetic dissection of a2-adrenoceptor functions in adrenergic versus nonadrenergic cells, Molecular Phar 2009, 75(5), p. 1160-1170.
Sato et al., In Silico Functional Profiling of Small Molecules and Its Applications, Journal of Medical Chemistry 2008, 51(24), 7705-7716 (Abstract).
Lehtimaeki et al., In vitro and in vivo profiling of fadolmidine, a novel potent a2-adrenoceptor agonist with local mode of action, European Journal of Pharmacology 2008, 599(1-3), 65-71 (Abstract).
Verbruggen et al., The effect of intravenous medetomidine on pupil size and intraocular pressure in normotensive dogs, Veterinary Quarterly 2000, 22(3), 179-180 (Abstract).
Sriram et al., Design and synthesis of alpha2 adrenoceptor agonists, Book of Abstracts, 213th ACS National Meeting, San Francisco, Apr. 13-17, 1997, MEDI-023, American Chemical Society: Washington, D.C. (Abstract).

(Continued)

*Primary Examiner* — Kara R McMillian
(74) *Attorney, Agent, or Firm* — Wood, Phillips, Katz, Clark & Mortimer

(57) ABSTRACT

The invention provides α-2 adrenergic receptor agonist compositions and methods for treating glaucoma and other intraocular conditions. The preferred α-2 agonist used in the inventive compositions and methods is dexmedetomidine.

15 Claims, No Drawings

OTHER PUBLICATIONS

Ogidigben et al., Comparative effects of alpha-2 and DA-2 agonists on intraocular pressure in pigmented and nonpigmented rabbits, Journal of Ocular Pharmacology 1993, 9(3), 187-99 (Abstract).

MacDonald et al., Comparison of the cardiovascular effects of the a2-adrenoceptor agonist, dexmedetomidine, in rats and rabbits, Drug Development Research 1993, 28(4), 473-477 (Abstract).

Jin et al., Ocular hypotensive effects of medetomidine and its analogs, Journal of Ocular Pharmacology 1991, 7(4) 285-296 (Abstract).

Laengle et al., GLC756 decreases TNF-alpha via an alpha2 and beta2 adrenoceptor related mechanism, Experimental eye research, Nov. 2006, 83(5), 1246-1251 (Abstract).

Stamer et al., Cultured human trabecular meshwork cells express functional alpha 2A adrenergic receptors, Investigative ophthalmology & visual science Nov. 1996, 37(12), 2426-2433 (Abstract).

Pate et al., Ophthalmic arachidonylethanolamide decreases intraocular pressure in normotensive rabbits, Current eyer research Sep. 1995, 14(9), 791-797 (Abstract).

Jin et al., Ocular a2-receptor subclasses and antiglaucoma efficacy, Journal of Ocular Pharmacology, 1994, 10(1), 359-369 (Abstract).

Potter et al., Review: Alpha2 and DA2 agonists as antiglaucoma agents: Comparative pharmacology and clinical potential, Journal of Ocular Pharmacology, 1990, 6(3), 251-257 (Abstract).

Kost et al., Procedural Sedation and Analgesia in the Pediatric Emergency Department: A Review of Sedative Pharmacology, Clinical Pediatric Emergency Medicine, Dec. 2010, 11(4), 233-243 (Abstract).

Penha et al., Retinal and ocular toxicity in ocular application of drugs and chemicals—Part I: Animal models and toxicity assays, Ophthalmic Research, Jul. 2010, 44(2), 82-104 (Abstract).

Mowafi et al., Effect of dexmedetomidine premedication on the intraocular pressure changes after succinylcholine and intubation, British Journal of Anaesthesia, Apr. 2008, 100(4), 485-489.

Mowafi et al., Remifentanil obtunds intraocular pressure rises associated with suxamethonium, British Journal of Anaesthesia, Sep. 2008, 101(3), 432-433.

Bielory, Chirality in ocular agents, Current Opinion in Allergy and Clinical Immunology, Oct. 2007, 7(5), 418-423 (Abstract).

Freeman, Hypoxic-ischaemic brain injury (HIBI) after cardiopulmonary arrest, Current Anaesthesia and Critical Care, 2007, 18(5-6), 261-276 (Abstract).

Crassous et al., Interest of a2-adrenergic agonists and antagonists in clinical practice: Background, facts and perspectives, Current Topics in Medicinal Chemistry, Jan. 2007, 7(2), 187-194 (Abstract).

Gentili et al., Agonists and antagonists targeting the different a2-adrenoceptor subtypes, Current Topics in Medicinal Chemistry, Jan. 2007, 7(2), 163-186 (Abstract).

Weber et al., Neuroprotective effects of a2-adrenergic receptor agonists, Drug News and Perspectives, Apr. 2007, 20(3), 149-154 (Abstract).

Loots, Agents for sedation in ophthalmic surgery: A review of the pharmacodynamics and clinical applications, Current Anaesthesia and Critical Care, 2006, 17(3-4), 179-190 (Abstract).

Robertson, Standing sedation and pain management for ophthalmic patients, Veterinary Clinics of North America—Equine Practice, Aug. 2004, 20(2), 485-497 (Abstract).

Ruffolo et al., a-Adrenoceptors, Pharmacology and Therapeutics, 1994, 61(1-2), 1-64 (Abstract).

Tripathi et al., Role of receptors in the trabecular meshwork of the eye as targeted to the development of antiglacoma therapy, Drug Development Research, 1992, 27(3), 1991-228 (Abstract).

Georgiou et al., Changes in NMDA receptor contribution to synaptic transmission in the brain in a rat model of glaucoma, Neurobiology of Disease, Sep. 2010, 39(3), 344-351 (Abstract).

Schoewald et al., Relationship between Steroid Permeability across Excised Rabbit Cornea and Octanol-Water Partition Coefficients, Journal of Pharmaceutical Scienses, Jun. 1978, 67(6), 786-788.

Chang et al., Improved Corneal Penetration of Timolol by Prodrugs as a Means to Reduce Systemic Drug Load, 1987, 28(3), 487-491.

Li et al., A Study of the Relationship between Cornea Permeability and Eye Irritation Using Membrance-Interaction QSAR Analysis, Toxicological Sciences, 2005, 88(2), 434-446.

Forster, et al., Adrenergic Alpha1, and Alpha2 Binding Sites are Present in Bovine Retinal Blood Vessels, Investigative Ophthalmology & Visual Science, 1987, 28(11), 1741-1746.

Donello et al., a2-Adrenoceptor Agonists Inhibit Vitreal Glutamate and Aspartate Accumulation and Preserve Retinal Function after Transient Ischemia, Journal of Pharmacology and Experimental Therapeutics, 2011, 296(1), 216-223.

Akasu et al., Reduction of the N-Type Calcuium Current by Noradrenaline in Neurones of Rabbit Vesical Parasympathetic Ganglia, Journal of Physiology, 1990, 426, 439-452.

Trendelenburg et al., a2-Adrenoceptor-mediated inhibition of cultured sympathetic neurons: changes in a2A/D-adrenoceptor-deficient mice, Naunyn-Schmiedeberg's Arch Pharmacology, 2011, 363, 110-119.

Dong et al., a2 Adrenergic Modulation of NMDA Receptor Function as a Major Mechanism of RGC Protection in Experimental Glaucoma and Retinal Excitotoxicity, Investigative Ophthalmology & Visual Science, Oct. 2008, 49(10), 4515-4522.

Saylor et al., Experimental and Clinical Evidence for Brimonidine as an Optic Nerve and REtinal Neuroprotective Agent, Arch Ophthalmol, Apr. 2009, 127(4), 402-406.

Shirasaka et al., Activation of a G Protein-coupled Inwardly Rectifying K+ Current and Suppression of lh Contribute to Dexmedetomidine-induced Inhibition of Rat Hypothalamic Paraventricular Nucleus Neurons, Anesthesiology, 2007, 107, 605-615.

Rosa et al., Brimonidine evokes hetrogenous vasomotor response of retinal arterioles: diminished nitric oxide-mediated vasodilation when size goes small, Am J Physiol Heart Cir Physiol 2006, 291, H231-H238.

Wirostoko et al., The Vascular Theory in Glaucoma, Glaucoma Today, Apr. 2009, 25-27.

Huang et al., The two sides of cytokine signaling and glaucomatous optic neuropathy, j ocul biol dis inform, 2009, 2, 98-103.

Hamasaki et al., Dual a2-Adrenergic Agonist and a1-Adrenergic Antagonist Actions of Dexmedetomidine on Human Isolated Endothelium-Denuded Gastroepiploic Arteries, Anesth Analg, 2002, 94, 1434-1440.

Paris et al., The Anesthetic Effects of Etomidate: Species-Specific Interaction with a2-Adrenoceptors, Anesth Analg. 2007, 105(6), 1644-1649.

Pertovaara, Antinociceptive Properties of Fadolmidine (MPV-24-26), a Novel a2-Adrenoceptor Agonist, CNS Drug Reviews, 2004, 10(2), 117-126.

Niemi et al., Synthesis, hydrolysis, and intraocular pressure lowering effects of fadolmidine prodrugs, International Journal of Pharmaceutics 2005, 29, 121-127.

Jaana Vartiainen et al, Dexmedetomidine-Induced Ocular Hypotension in Rabbits With Normal or Elevated Intraocular Pressures, Investigative Ophthalmology & Visual Science, vol. 33, No. 6, May 1992, pp. 2019-2023.

* cited by examiner

COMPOSITIONS AND METHODS FOR TREATMENT OF GLAUCOMA

This application is a continuation-in-part of U.S. patent application Ser. No. 13/365,138, filed on Feb. 2, 2012, which is a continuation-in-part of U.S. patent application Ser. No. 12/931,632, filed on Feb. 3, 2011. The entire teachings of the above-referenced applications are incorporated herein by reference.

BACKGROUND OF THE INVENTION

Glaucoma is a multifactorial disease which encompasses a spectrum ranging from elevated intraocular pressure (IOP) to reduced vascular perfusion of the optic nerve.

While many factors have been implicated as contributing causes of glaucoma, currently existing treatments for glaucoma have limited effectiveness in lowering IOP and/or are accompanied by a number of side effects, such as fatigue, sedation, lid allergy, topical allergy, and/or redness.

Because of the side effects, an additional major problem in glaucoma therapy is patient compliance in taking medications as prescribed. It is believed that many of these side effects and suboptimal efficacy of the existing treatments are unintended consequences of alpha-1 (α-1) receptor induction from treatment with alpha agonists.

Over 40% of glaucoma patients require two or more drugs for satisfactory control of their intraocular pressure. Of these, the prostaglandins/prostanoids, including Xalatan® (latanoprost), Travatan® (travoprost) and Lumigan® (bimatoprost), are the leading drugs due to their profound reduction of IOP, typically above 30% in ocular hypertensive eyes (21 mm Hg or greater), and long duration improvement in uveoscleral outflow. To have the greatest effect, the two drugs should have different mechanisms of action.

Brimonidine, a known alpha-2 (α-2) adrenergic receptor agonist, typically causes moderate peak IOP reduction of about 20-25% in ocular hypertensive eyes and 6-18% in normotensive eyes (less than 21 mm Hg). Its peak effect is within 2-3 hours of instillation, its duration of effect is typically less than 12 hours, and its moderate efficacy usually requires dosing of 2-3 times a day. It is one of the leading secondary drugs, with a mechanism of action of aqueous suppression that complements the prostaglandin/prostanoids uveal scleral outflow enhancement for significant additive benefit. Currently, brimonidine is the only commercially available alpha-2 agonist, proving safer and/or more effective than predecessors against which it has been compared, including clonidine (fewer instances of systemic hypotension and/or bradycardia), apraclonidine (fewer instances of tachyphylaxis), and dexmedetomidine (less systemic sedation, greater IOP reduction efficacy).

However, brimonidine may induce substantial local side effects in 10-25% of users, such as conjunctival hyperemia (redness), blepharitis, allergy, conjunctival edema, conjunctival follicles, foreign body sensation, burning, or blurring. These side effects were only modestly improved by recent brimonidine formulations, resulting in somewhat reduced concentrations with increased intraocular absorption at more alkaline pH (Alphagan® P, Allergan Pharmaceuticals). In general, α-2 agonists, including brimonidine, clonidine and dexmedetomidine, induce substantial systemic effects if absorbed into the circulation, and are specifically known to decrease blood pressure (hypotension) and lower the heart rate (bradycardia). Further, many α-2 agonists, particularly the more lipophilic drugs such as clonidine and dexmedetomidine readily cross the blood brain barrier and thereby induce potent sedative effects. Dexmedetomidine, in particular, is a potent intravenous sedative, and side effects such as drowsiness, shortness of breath, dizziness, headache, hypotension, bradycardia, and mood depression are common to all α-2 agonists depending on their degree of systemic absorption. Brimonidine in particular produces topical lid and conjunctival allergy, dryness, and redness in well over 10% of patients. These side effects contribute to suboptimal compliance with brimonidine, which also negatively affects treatment.

Dexmedetomidine in phosphate buffer at pH 6.4-6.5 has been studied in normotensive and artificially elevated eye pressure rabbits. U.S. Pat. No. 5,304,569 (Lammintausta) describes the use of 0.02% dexmedetomidine in normotensive rabbits resulted in equal pressure reduction (100%) in the nontreated (contralateral) eye and the treated eye, a known side effect indicative of high systemic absorption. Vartiainen et al demonstrated that dexmedetomidine at 0.05% in normotensive rabbits results in a pressure reduction of 4.75 mm Hg, with a peak effect at about 2 hours. (*Inv Oph. & Vis Sci., Vol. 33, No. 6, May 1992, Dexmedetomidine-Induced Ocular Hypotension in Rabbits With Normal or Elevated Intraocular Pressures Vartiainen* et. al). The comparison of the use of brimonidine tartrate 0.10% solution vs. dexmedetomidine in normotensive rabbits demonstrates a higher peak of about 6.2 mm Hg with brimonidine, a longer duration with peak of about 3 hrs vs. 2 hours for dexmedetomidine, and lower systemic absorption with brimonidine, with contralateral (nontreated eye) IOP reduction of only about 10% vs. about 100% for dexmedetomidine compared to the treated eye (Center for Drug Evaluation and Research Number 21-770, Pharmacology Review, brimonidine tartrate 0.1%, Allergan Pharmaceuticals). For over two decades, brimonidine has been the only commercially available α-2 agonist, due to its demonstrated combination of superior IOP reduction with greatly reduced risk of systemic side effects versus all other α-2 agonists attempted for this purpose, despite its less than optimal side effect profile and modest efficacy relative to prostaglandins/prostanoids.

Accordingly, there is a need for novel formulations of alpha-2 (α-2) agonists for the treatment of glaucoma which would have less systemic absorption, minimal, if any, cross-activation of α-1 receptors, improved intraocular retention with more effective IOP lowering and duration, and with significantly reduced or eliminated side effects of conventional α-2 agonists, such as burning, stinging, sedation and redness. In addition, an improved cosmetic appearance via both reduced redness and a cosmetically pleasing whiter shading of the eye may be important in reducing the rate of patients noncompliance.

BRIEF SUMMARY OF THE INVENTION

The present invention provides compositions and methods effective for the treatment of glaucoma in a patient in need thereof. Preferably, the compositions of the invention are formulated to prevent sedation, eliminate or reduce redness, eliminate or reduce ocular allergy, as well as significantly reduce intraocular pressure.

In some embodiments, the provided compositions may also have an eye whitening effect. Most preferably, the compositions include all of the above benefits and also have neuroprotective benefits and may be used for optic nerve protection, including the treatment of neurodegenerative conditions, such as ischemic optic neuropathy, diabetic retinopathy, optic ischemia, retinal vascular ischemia, and other optic neuropathies, particularly those involving retinal ganglion cells and/or axons at or near the optic nerve lamina.

The present invention optimizes α-2 agonist corneal permeation utilizing a highly selective α-2 agonist which is formulated to optimize intraocular penetration at a lipophilicity of preferably Log P 2.5 or greater and range of topical lipophilicity based on the pH and optional buffering of the formulation that may range from 0.73 to 3.08 (measured relative to pH as the Log D value). Further, the improved formulations allow for reduced α-1 agonist activity and reduced systemic absorption, allowing for a more lipophilic alpha 2 agonist for topical use.

The preferred compositions of the invention employ selective α-2 adrenergic receptor agonists.

In a preferred embodiment, the invention provides novel formulations of dexmedetomidine, which are surprisingly found to be much more effective for the treatment of glaucoma than brimonidine. These novel inventive formulations share some or all of the following characteristics:

a) a high selectivity for α-2 over α-1 adrenergic receptors, such as 1000:1 or greater; more preferably 1500:1 or greater; and even more preferably 2000:1 or greater;
b) a high degree of intraocular lipophilicity as measured by the Log P, the equilibrated intraocular pH at 7.4, with an octanol-water partition coefficient Log P of between about 1.5 and 4.0; and more preferably between about 2.50 and 3.50 at physiologic pH; and
c) include a poloxamer at specified concentration range, and one or more specific viscosity enhancers (also interchangeably referred to as "gelling agents").

In one embodiment, the invention provides a pharmaceutical composition comprising:

i. an α-2 adrenergic receptor agonist at a concentration from between about 0.0125% to about 0.125% weight by volume, wherein said α-2 adrenergic receptor has a Log P value of 2.0 or greater and has a binding affinity of 950 fold or greater for α-2 over α-1 adrenergic receptors;
ii. a salt;
iii. a poloxamer at a concentration of between 3% and 12% weight by volume or less; and
iv. a viscosity enhancer,
    wherein said pharmaceutical composition has a viscosity of between 50 and 300 cps, and
    wherein said pharmaceutical composition is effective for the treatment of glaucoma in a patient in need thereof.

A preferred α-2 adrenergic receptor agonist is dexmedetomidine.

Preferably, dexmedetomidine is at a concentration from between about 0.035% and 0.12% weight by volume, and more preferably between about 0.050% and 0.10%.

In one embodiment, the salt selected from the group consisting of sodium chloride, citrate, mesylate, hydrobromide/bromide, acetate, fumarate, sulfate/bisulfate, succinate, phosphate, maleate, nitrate, tartrate, benzoate, carbonate, and pamoate.

Preferably, the salt is sodium chloride (e.g., a saline solution).

In one embodiment, the viscosity enhancer is selected from carboxymethyl cellulose, methylcellulose, hydroxymethyl cellulose, hydroxypropylmethyl cellulose, hydroxyethyl cellulose, polyethylene glycol, dextran, povidone, alginic acid, guar gum, acacia, veegum, gelatin, chitosan, carbopol, locust bean gum, acidic polycarbophil, dextran, pectin, povidone, polyvinylpyrrolidone, polyvinyl alcohol, and hyaluronic acid.

In a preferred embodiment, the viscosity enhancer is carboxymethyl cellulose.

Preferably, the poloxamer is present at concentration range of 3% to 10% by weight; and more preferably, at 5% to 6% by weight.

Preferably, the poloxamer is selected from the group consisting of poloxamer 407, poloxamer 188, and combinations thereof.

In one embodiment, the pharmaceutical composition may further comprise a buffer which may be selected from the group consisting of citrate buffer, borate buffer, maleate buffer, succinate buffer, phosphate buffer, acetate buffer, sorbate buffer and carbonate buffer.

In one embodiment, the buffer is at a concentration between 1 mM and 100 mM.

In one embodiment, the pharmaceutical composition has an octanol-water partition coefficient Log D of between about 0.70 and about 2.98, or preferably between about 1.25 and 2.50.

Accordingly, in one embodiment the invention provides a pharmaceutical composition comprising i. dexmedetomidine is at a concentration from between 0.02% and about 0.12% weight by volume; and more preferably 0.050% to 0.10% weight by volume.
ii. sodium chloride at a concentration of 0.25% to 0.50%;
iii. a poloxamer at a concentration of between 3 and 12% weight by volume or more preferably, at 5 to 6%;
iv. carboxymethyl cellulose (CMC), and
wherein said pharmaceutical composition has a viscosity of between 20 and 500 cps and more preferably 50 and 150 cps.

In one embodiment, the pharmaceutical compositions of the invention may further comprise a mucoadhesive, which may be present at a concentration from between about 0.5% and about 10% weight by volume.

In one embodiment, the mucoadhesive is selected from the group consisting of carbapols, xanthan gums, and cellulose derivatives.

The invention also provides methods of treating glaucoma and/or posterior pole ocular neurodegenerative conditions and/or dry eye in a patient in need thereof comprising administering to said patient the pharmaceutical compositions of the invention.

The invention also provides a vehicle formulation for drug delivery, wherein said vehicle formulation comprises a poloxamer, hypotonic saline, and a viscosity enhancer, at the same concentrations and ranges as previously recited.

The invention also provides an artificial tear solution comprising:

i. a hypotonic salt or sterile water;
ii. a poloxamer at a concentration of 12% weight by volume or less; and
iii. a viscosity enhancer, and
wherein said pharmaceutical solution has a viscosity of between 25 and 500 cps.

DETAILED DESCRIPTION OF THE INVENTION

Definitions

The term "α-1 adrenergic receptor" refers to a G-protein-coupled receptor (GPCR) associated with the $G_q$ heterotrimeric G-protein.

The term "α-2 adrenergic receptor" refers to a GPCR associated with the $G_i$ heterotrimeric G-protein.

The term "selective α-2 adrenergic receptor agonists" encompasses all α-2 adrenergic receptor agonists which have a binding affinity of 1000 fold or greater for α-2 over α-1 adrenergic receptors, and more preferably 1500 fold or greater. The term also encompasses pharmaceutically acceptable salts, esters, prodrugs, and other derivatives of selective α-2 adrenergic receptor agonists.

The term "dexmedetomidine" encompasses, without limitation, dexmedetomidine salts, esters, prodrugs and other derivatives.

The term "prodrug" refers to a compound that may be converted under physiological conditions to a biologically active compound.

As used herein, the term "composition" is intended to encompass a product comprising the specified ingredients in the specified amounts, as well as any product which results, directly or indirectly, from a combination of the specified ingredients in the specified amounts.

The terms "treating" and "treatment" refer to reversing, alleviating, inhibiting, or slowing the progress of the disease, disorder, or condition to which such terms apply, or one or more symptoms of such disease, disorder, or condition.

The terms "preventing" and "prevention" refer to prophylactic use to reduce the likelihood of a disease, disorder, or condition to which such term applies, or one or more symptoms of such disease, disorder, or condition. It is not necessary to achieve a 100% likelihood of prevention; it is sufficient to achieve at least a partial effect of reducing the risk of acquiring such disease, disorder, or condition.

The term "significant side effects" refers to substantial side effects of the treatment which include at least: a) sedation of a patient such that the patient feels sedated and becomes impaired or b) visually noticeable increase in redness of a patient's eye due to hyperemia.

The term "medicamentosa" refers to the inflammatory sequelae of α-1 agonist topical medications, particularly following topical ocular or nasal delivery, such as the development of increased vasodilation and hyperemia, in its less severe form referred to as "rebound".

The terms Poloxamer 407 and Pluronic® F127 are used interchangeably.

EMBODIMENTS OF THE INVENTION

The present invention provides compositions and methods effective for the treatment of glaucoma in a patient in need thereof. Preferably, the compositions of the invention are formulated to prevent sedation, eliminate or reduce redness, eliminate or reduce ocular allergy, as well as significantly reduce intraocular pressure.

Specifically, the provided formulations comprise the following ingredients:
a) a selective α-2 agonist, preferably dexmedetomidine, at a concentration between about 0.0125% to about 0.125% weight by volume;
b) a salt (e.g., hypotonic saline, NaCl);
c) a poloxamer (which may be selected from various grades of poloxamer, including but not limited to 407 and 188) at a concentration at about 12% or less, and preferably between about 3% and 10%; and more preferably between about 5% and 6%;
d) a viscosity enhancer, preferably carboxymethyl cellulose (CMC) at 0.25-1.0%, and more preferably at 0.075%;
wherein the viscosity of the provided formulation is between 25 and 500 cps, and more preferably about 50 and 200 cps.

In one embodiment, the invention provides a pharmaceutical composition comprising:

i. dexmedetomidine at a concentration from between about 0.0125% to about 0.125% weight by volume;
ii. a salt;
iii. a poloxamer at a concentration of 12% weight by volume or less; and
iv. a viscosity enhancer,
wherein said pharmaceutical composition has a viscosity of between 50 and 500 cps, and
wherein said pharmaceutical composition is effective for the treatment of glaucoma in a patient in need thereof.

Preferably, dexmedetomidine is at a concentration from between about 0.035% to 0.10% weight by volume.

Preferably, the pH of the provided compositions is within a range of 4.0 to 8.0, and more preferably about 5.0 to 6.0.

In one embodiment, the salt selected from the group consisting of sodium chloride, citrate, mesylate, hydrobromide/bromide, acetate, fumarate, sulfate/bisulfate, succinate, phosphate, maleate, nitrate, tartrate, benzoate, carbonate, and pamoate.

Preferably, the salt is sodium chloride (e.g., a saline solution).

In one embodiment, the viscosity enhancer is selected from carboxymethyl cellulose, methylcellulose, hydroxymethyl cellulose, hydroxypropylmethyl cellulose, hydroxyethyl cellulose, polyethylene glycol, dextran, povidone, alginic acid, guar gum, acacia, veegum, gelatin, chitosan, carbopol, locust bean gum, acidic polycarbophil, dextran, pectin, povidone, polyvinylpyrridone, polyvinyl alcohol, and hyaluronic acid.

In a preferred embodiment, the viscosity enhancer is carboxymethyl cellulose.

Preferably, the poloxamer is present at concentration range of 3% to 10% by weight; and more preferably, at 5% to 6% by weight.

Preferably, the poloxamer is selected from the group consisting of poloxamer 407, poloxamer 188. However, other poloxamers and/or combinations of various poloxamers can be used for the purposes of the present invention.

In a preferred embodiment, the compositions of the invention may include the following components:
1) dexmedetomidine at a concentration of between 0.0125% and 0.125%, most preferably 0.035% to 0.10%, weight by volume;
2) sodium chloride at a concentration of between 0 to 0.75%, more preferably 0.25% to 0.50%.
3) a poloxamer, preferably, Poloxamer 407 (Pluronic® F127) or 188 or combination thereof, at a concentration of between 1% and 10%, more preferably, 5% to 6%;
4) carboxymethyl cellulose high blend (CMC), at a concentration of between 0.25% and 1%; more preferably 0.62% to 0.75%; and
5) optionally, benzalkonium chloride (BAK) at a concentration of between 0.01% and 0.02%; preferably at 0.02%.

In one embodiment, the pharmaceutical composition may further comprise a buffer, which may be selected from the group consisting of citrate buffer, borate buffer, maleate buffer, succinate buffer, phosphate buffer, acetate buffer, sorbate buffer and carbonate buffer.

In one embodiment, the buffer is at a concentration between 1 mM and 100 mM, more preferably 4 mM to 10 mM.

In one embodiment, the pharmaceutical composition has an octanol-water partition coefficient Log D of between about 0.70 and about 2.20, and preferably between about 1.25 and 2.00.

In one embodiment, the pharmaceutical compositions of the invention may further comprise a mucoadhesive, which may be selected from the group consisting of carbapols, xanthan gums, and cellulose derivatives. However, other gums and/or gels, and/or viscosity enhancers can also be used for the purposes of the present invention.

In one embodiment, the mucoadhesive is at a concentration from between about 0.5% and about 1.0% weight by volume.

The inventive formulations may also optionally include other ingredients, such as corneal penetration enhancers and others.

The invention also provides a method of treating glaucoma and/or posterior pole ocular neurodegenerative conditions in a patient in need thereof comprising administering to said patient the pharmaceutical compositions of the invention.

Additionally, the inventive compositions may provide optic nerve protection, retinal ganglion cell neuroprotection, an increase in α-2 agonist concentration in the inner retinal plexiform, and additional neuroprotective benefits. They may also increase the outflow at the trabecular meshwork which is populated with endothelial cells and believed to be populated with α-2a receptors in humans.

In addition, the methods and compositions of the invention may be used to reduce eye redness and/or increase eye whiteness in subjects in need thereof.

Unexpected Results of Using the Specific Combinations of the Ingredients

The presence of these four ingredients at the recited ranges (a selective α-2 agonist, a salt; a poloxamer at 12% or less; and another viscosity enhancer, preferably CMC) is essential for providing effective pharmaceutical formulations which provide a stronger and more durable IOP reduction than prior art brimonidine or dexmedetomidine formulations. Unless these ingredients are present, other viscosity enhancers and other excipients are ineffective, and/or substantially reduce the α-2 agonist activity of dexmedetomidine (and, possibly, of other α-2 agonists), and/or do not reduce systemic absorption or other side effects of dexmedetomidine formulations, in particular, sedation.

It was surprising that the discovered ranges and combinations were found to be most effective. None of these formulation ingredients by itself provides the required sustained release and reduced systemic absorption. Based on prior art, one would expect that clonidine and dexmedetomidine would be inferior glaucoma drugs than less lipophilic brimonidine or apraclonidine.

Further, it has been found that a poloxamer alone, regardless of concentration, is not only ineffective for the purposes of the present invention in terms of increased efficacy, but it also creates severe stinging on topical application, whether it is buffered or non-buffered, and regardless of pH.

It would have been expected that the concentration of a poloxamer should be within the 15% to 25% range, at which gelling effect at room temperature is known to occur and/or at the physiologic range of tonicity enhancers; however, it has been discovered that a poloxamer is effective in the provided combinations when it is present at 12% or less, and preferably at more than 3% but less than 10%. When poloxamer is present at a concentration of 15% or greater or less than 2%, the compositions are surprisingly less effective or ineffective.

It was also surprising and unexpected that other gelling agents, such as Carbopol® 954 and/or xanthan gums, could not be used instead of a poloxamer. One would have expected that these agents be interchangeable.

Further, the use of viscosity enhancers at too low concentrations resulted in surprisingly more side effects and reduced efficacy. It has also been found that the use of viscosity enhancers by themselves (i.e., without a poloxamer) results in much less effective formulations with more side effects.

Further, it has been surprisingly found that when the tonicity of the provided formulations is at 0 to 200 mOsm/kg, and preferably at 50 to 150 mOsm/kg, a sustained wetting/lubricating effect will result with minimal blurring and the greater comfort for the patients. Typically, an ophthalmic vehicle requires 280-310 mOsm/kg, which is achieved through the use of electrolytes or polyols (e.g. mannitol).

Advantages of the Provided Compositions and Methods

The provided compositions and methods are effective for the treatment of glaucoma. Preferably, the compositions of the invention are formulated to prevent sedation, eliminate or reduce redness, may increase duration of therapeutic action and reduce the incidence of rebound hyperemia and/or other allergic reaction, as well as more significantly reduce intraocular pressure than prior art formulations of α-2 agonists.

It has been surprisingly found that the provided combinations of the ingredients result in up to a two-fold increased duration effect, and about a two-fold or greater peak IOP reduction for dexmedetomidine versus similar dexmedetomidine formulations (e.g., dexmedetomidine in phosphate buffer pH 6.4-6.5). They also provide a five to six-fold decrease in contra-lateral (non-treated eye) IOP reduction vs. ipsilateral (treated eye effect), reflecting greatly reduced systemic absorption affecting the non-treated eye. In non-inventive dexmedetomidine formulations (dexmedetomidine at 0.025% to 0.05% in phosphate buffer at pH 6.4-6.5), contra-lateral eye IOP is 90-100% of the IOP of the treated eye, due to very high systemic absorption (vs. about 10% systemic absorption with the compositions of the present invention).

In a preferred embodiment, the formulations of the present invention provide the IOP reduction of 40% at 4 hours in a treated eye. The IOP reduction in the treated eye is greater than that found for the most optimized formulation of brimonidine (Alphagan® P at 0.1%, pH 7.4 or greater), which is about 20% in a treated eye.

Every 1 mm Hg reduction in IOP may result in substantial prevention of visual field loss. The longer duration of effect of the present invention creates a substantial effect over a 24 hour period, while a single dose of the conventional brimonidine formulations provides the IOP reduction effect for only about 12 hours or less.

The provided compositions may also improve cosmetic appearance of the treated eyes (for example, by increasing whiteness and providing additional whitening), resulting in improved patients' compliance. A common side effect of glaucoma drugs and, particularly, brimonidine, is eye redness (20-25% rebound redness with long term use of brimonidine), and compliance is a key problem. For this reason, it is believed that reduction of redness, and/or cosmetic whitening achieved with the provided compositions are likely to substantially improve compliance. The invention also provides improved wetting and comfort, lasting up to an hour after instillation.

In addition, it has been surprisingly discovered that novel formulations provide a much greater comfort, a greater eye wetting and lubrication action, significantly fewer topical side effects than brimonidine, and result in few, if any, systemic effects. Thus, the provided formulations are significantly superior to conventional brimonidine or dexmedetomidine formulations. This surprising discovery was contrary to over 20 years of prior art findings that brimonidine was more effective than dexmedetomidine.

Thus, in some embodiments, the beneficial effects of the provided compositions include:

1) onset within one hour;
2) peak effects of over 30%, and as great as 40% in normotensive eyes;
3) reduction over normotensive baseline mean IOP of about 15.5 to a mean IOP of about 9.3;
4) peak effects at about 3.5-4 hours, compared to 2 to 2.5 hours for brimonidine;
5) prolonged action with great comfort and minimal to absent stinging, eye ache, or lid irritation;
6) a strong lubricating-wetting effect for nearly one hour after instillation with only transient blurring up to one minute;
7) improved cosmetic appearance via reduction of redness and in some cases cosmetic whitening;
8) less systemic absorption (only about 16% contralateral (non-treated) eye IOP reduction with inventive formulations versus much higher systemic absorption with prior art formulations of dexmedetomidine;
9) reduction of topical and systemic side effects associated with conventional formulations of α-2 agonists (such as apraclonidine and brimonidine), including but not limited to reduced incidence of: oral dryness, ocular hyperemia, burning and stinging, headache, blurring, foreign body sensation, conjunctival follicles, ocular allergic reactions, ocular pruritus, corneal staining/erosion, photophobia, eyelid erythema, ocular ache/pain, ocular dryness, tearing, upper respiratory symptoms, eyelid edema, conjunctival edema, dizziness, blepharitis, ocular irritation, gastrointestinal symptoms, asthenia, abnormal vision, muscular pain, lid crusting, conjunctival hemorrhage, abnormal taste, insomnia, conjunctival discharge, depression, hypertension, anxiety, palpitations/arrhythmias, nasal dryness and syncope.

Some of the characteristics which are important for the provided compositions include selectivity for α-2 versus α-1 adrenergic receptors, lipophilicity, tonicity and solubility.

Selectivity for α-2 Versus α-1 Adrenergic Receptors

The selective α-2 adrenergic receptor agonists have binding affinities ($K_i$) for α-2 over α-1 receptors of 1000:1 or greater; more preferably 1500:1 or greater; and even more preferably 2000:1 or greater. It is well within a skill in the art to design an assay to determine α-2/α-1 functional selectivity. For example, potency, activity or $EC_{50}$ at an α-2A receptor can be determined by assaying for inhibition of adenylate cyclase activity. Furthermore, inhibition of adenylate cyclase activity can be assayed, without limitation, in PC12 cells stably expressing an α-2A receptor such as a human α-2A receptor. Additionally, potency, activity or $EC_{50}$ at an α-1A receptor can be determined by assaying for intracellular calcium. Intracellular calcium can be assayed, without limitation, in HEK293 cells stably expressing an α-1A receptor, such as a bovine α-1A receptor.

For the purposes of the present invention, it is desired to avoid or minimize triggering of α-1 receptors. Even a small critical threshold achieved of undesired α-1 receptor recruitment creates sufficient generalized vasoconstriction, microinflammatory change, and/or pro-inflammatory cytokine release to reduce effectiveness of the α-2 receptor induced positive treatment effects. As all α-2 agonists known have a relative affinity for α-2 vs. α-1, this partial affinity is measure by the ratio of α-2 to α-1 receptor induction, where the multiplied product of the degree of selective α-2 affinity—the α-2/α-1 ratio×the concentration C % determines that actual total pool of both α-2 and α-1 receptors induced.

The discovered range of necessary high selectivity, high lipophilicity and relatively low concentration of induced α-1 effects completely alters the IOP efficacy and side effect profile of α-2 agonist drugs. Accordingly, when these α-2 agonists are used for the treatment of glaucoma, they greatly reduce IOP and provide eye whitening without significant side effects believed to be associated with α-1 receptors, such as rebound hyperemia.

In some embodiments, compositions and methods of the invention include selective α-2 adrenergic receptor agonists which have $K_i$ for α-2 over α-1 receptors of 1500 fold or greater and have an octanol-water partition coefficient of about Log P 2.50-3.0 adjusted however for topical pH (Log D) to be between 0.75 and 3.08. Tears and intraocular fluids are physiologic at pH 7.4, which is equal to pH at Log P and, according to the precepts of the present invention, confers IOP reduction benefits. Corneal physiology requires a delicate and different octanol-water Log value (called Log D, determined by the pH of the formulation), so that the formulations are able to not only penetrate the lipophilic corneal epithelium and inner endothelium, but also penetrate the hydrophilic middle stromal layer.

In yet other embodiments, compositions and methods of the invention include selective α-2 adrenergic receptor agonists which have $K_i$ for α-2 over α-1 receptors of 1000 fold or greater and are at a concentration from between about 0.0035% to about 0.035% weight by volume.

Brimonidine, guanfacine, guanabenz, dexmedetomidine and fadolmidine are some of the sufficiently highly selective α-2 agonists to satisfy the selectivity requirement. However, of these highly selective α-2 agonists, only dexmedetomidine satisfies other additional preferred formulation characteristics of the present invention, such as lipophilicity. Other α-2 agonists, such as clonidine, may be sufficiently lipophilic but lack sufficient selectivity.

It is currently believed that the most preferred selective α-2 adrenergic receptor agonist suitable for purposes of the invention is dexmedetomidine as either the HCl salt, or as the citrate salt. Other salts may similarly be substituted for the HCl.

Accordingly, in some embodiments, compositions and methods of the invention include dexmedetomidine, or another selective α-2 adrenergic receptor agonist, at a concentration from between about 0.0125% to about 0.125% weight by volume; more preferably, between about 0.025% to about 0.125% weight by volume; and even more preferably between about 0.045% and about 0.10% weight by volume.

It is believed that new α-2 agonists can be synthesized to meet the requirements of the present invention.

Lipophilicity

For any given ophthalmic drug, an optimal lipophilicity exists to maximize requisite penetration into the lipophilic cornea surface epithelium and, to a lesser extent, inner layer endothelium. If a drug is too hydrophilic, the epithelium becomes an impenetrable barrier. If a drug is too lipophilic, the drug cannot pass through the more hydrophilic stroma.

Lipophilicity may be measured, for example, using known measurements, such as Log P (log $K_{OW}$) derivation of the octanol-water partition coefficient and/or, a closely related coefficient, XLogP3-AA. See, for example, Tiejun Cheng et al, *Computation of Octanol-Water Partition Coefficients by Guiding an Additive Model with Knowledge*, J. Chem. Inf. Model., 2007, 47 (6), pp 2140-2148. These measurements represent the intraocular lipophilicity value of topical drugs for intraocular delivery (i.e., once the drug permeates into the anterior chamber and is at a pH of 7.4). A person of ordinary skill in the art is well familiar with these measurements. Thus, the Log P value is the octanol-water coefficient at pH 7.4, i.e., physiologic pH.

It was discovered in prior art that increasing the pH results in a better lipophilicity profile, making brimonidine mildly lipophilic on topical instillation and resulting in a better corneal penetration. For weak base α-2 agonists, such as brimonidine and dexmedetomidine, the more alkaline pH, the more the equilibrium between ionized base releasing H+ and non-ionized base shifts to the left (non-ionized), resulting in a more lipophilic compound. This is particularly true for α-2 agonists with pKa values of near or greater than 7.0, as is the case for brimonidine and dexmedetomidine. This is because at a more alkaline pH, more of the compound is present in a non-ionized form, and conversely therefore, at more acidic pH more of a drug is ionized and less lipophilic. Usually, Log P and/or XLogP3-AA are measured when the formulation at issue is or will be at the physiologic pH of about 7.4.

For a majority of drugs a general trend of Log P values from 2.0 to 3.0 is thought to be the best range of lipophilicity, though some of the best absorbing drugs range from 1.00 to about 2.50. Since each drug has its own Log P, and is not always amenable to stable Log D/pH manipulation, little is known about how each drug might be further optimized for topical delivery. The Log P value is highly drug/drug subclass specific, and while predictive software algorithms have been developed, there is no completely accurate means for determining the ideal Log P value for a proposed drug formulation to optimize intraocular penetration.

The range between +2.0 and +3.0 typically allows for the best compromise between: a) the need for a highly lipophilic drug to penetrate the lipophilic corneal epithelium, and to a lesser extent, the very thin inner corneal membrane called Descemet's membrane, and b) a highly hydrophilic drug to penetrate the stroma, which is the middle layer of the corneal "sandwich" that must be penetrated for effective ophthalmic absorption.

The disclosed combination of a poloxamer, a viscosity enhancer and a hypotonic solution at the disclosed concentration ranges provides a delivery vehicle for dexmedetomidine (and, it is believed, for other mild to highly lipophilic drugs) that is independent of pH and largely independent of the individual drug's lipophilicity.

The optimal pH of the provided formulations (i.e., the topically delivered pH of the formulation before physiologic equilibration to pH 7.4) is such pH that results in a Log "D" value for the drug (the initial topical lipophilicity) of between 0.75 and 3.08, and more preferably between 0.92 and 2.98, representing the maximum pH range of 4.0 to 8.0, and the preferred pH range of 4.5 to 7.0 for optimal comfort and stability.

Noticeably, for some dexmedetomidine formulations, increased stinging has been observed, particularly at pH of 4.0 to 7.0, and particularly pH 4.0 to 4.5. Further, it has been discovered that certain buffers added to dexmedetomidine in 0.9% NaCl render the drug less effective: particularly, phosphate buffer in its pH range of 6.0 to about 6.4.

However, it has been discovered that the topical application of the inventive formulations (i.e., those formulations including all of the required ingredients at the required concentrations), is not pH sensitive. Further, the efficacy of the inventive formulations no longer appears to be reduced by any particular buffers, including phosphate buffer. It is believed that the specific combination of the ingredients in the inventive formulations confers this pH independence and increased solubility range on a variety of active drugs, both for glaucoma and other purposes, as well as provides increased absorption and reduced systemic side effects; including but not limited to steroidals, nonsteroidals, anti-infectives (anti-virals and antimicrobials), and macular degeneration drug treatments such as anti-VEGF.

The preferred Log P (and XLogP3-AA) values—those that define intraocular performance according to the present invention—that are suitable for the purposes of the invention are between about 1.00 and 4.50; and more preferably, between about 2.0 and 3.50. If the selectivity of a specific α-2 agonist is substantially above 1000:1 (for example, 1500:1), additional advantages are believed to be conferred via greater α-2 agonist binding and reduced α-1 agonist induced ischemia. For example, optic nerve damage progression is known to be highly sensitive to circulation change and ischemia. Because the drug is used over an extended period of time, even small reductions in unintended α-1 agonist-induced ischemia may be beneficial. Thus it is a discovery of the present invention that the α-2 agonist intraocular lipophilicity as represented by Log P, and selectivity as represented by the α-2:α-1 receptor recruitment ratio, appear to be very important for greater efficacy of an α-2 agonist glaucoma drug. If the selectivity is above, for example, 2000:1, then it is possible that this agonist may be effective for the purposes of the invention at slightly reduced lipophilicity, and vice versa.

Table 1 provides known XLogP3-AA values (a more accurate Log P) and α2/α1 binding affinities for several α-2 agonists.

TABLE 1

| α-2 Agonist | XLogP3AA | α2:α1 |
|---|---|---|
| Brimonidine (pH 6.0-8.0) | 0.6-1.8 | 976 |
| Guanfacine | 2.0 | |
| Guanabenz | 1.7 | |
| Dexmedetomidine | 3.1 | 1620 |
| Fadolmidine pivalyl prodrug ester | 1.8 | |
| Fadolmidine | ≦1.2 | |
| Methoxamine | 0.5 | |
| Oxymetazoline | 2.9 | 50 |
| Epinephrine | −1.4 | |
| Clonidine | 1.6 | 200 |
| Apraclondine | 1.3 | 150 |
| Mivazerol | 1.1 | |
| Xylazine | 2.8 | 160 |
| Methyl Dopa | −1.9 | |
| Lofexidine | 2.6 | <300 |

Table 1 demonstrates that among the listed α-2 agonists, only dexmedetomidine has an optimal combination of high lipophilicity (XLogP3-AA) and highly selective α2:α1 coefficient. However, it is possible that formulations including other α-2 agonists can be achieved which meet the defined requirements of the present invention in both selectivity and lipophilicity categories.

In some embodiments, dexmedetomidine, or another selective α-2 adrenergic receptor agonist, has Log P at an intraocular pH 7.4 of about 3.10; preferably, between about 2.0 and 5.00; and more preferably between about 2.75 and 3.50

As Log D refers to a lipophilicity value at a given pH, this measurement is especially useful to determine the level of topical lipophilicity and resultant corneal permeability of a topical composition through the highly lipophilic corneal epithelium.

Normally, higher Log P values, such as 3.0 or greater, are constrained by the highly hydrophilic stroma, and therefore a compromise lipophilicity of 1.0 to 3.0 and more preferably 1.5 to 2.5 is preferred for most ophthalmic topical drugs. Corneal permeability is a complex event, which may be affected by polar surface area, H+ donor activity, bond rotation, and active transport phenomenon.

It is a discovery of the present invention that the Log D values of between about 0.75 and about 2.20, and more particularly between about 1.00 and about 1.50, are preferred for increased corneal permeation of dexmedetomidine and other similar α-2 agonists in normal saline, preferably below the pH of 6.4 to 6.5, and that the "vehicle" of the present invention including poloxamer, viscosity enhancer and hypotonic saline or sterile water greatly reduces and likely totally eliminates such pH limitations.

When the selective α-2 agonist is dexmedetomidine, the optimal Log D value is from 0.75 to 2.2, and more preferably is about 1.00 to 2.00 at a topical pH of about 4.7 to 6.0.

Tonicity

For purposes of comfort topical delivery, ophthalmic drugs typically require about 275 to 320 mOsm/kg tonicity. A variety of tonicity enhancers, including but not limited to electrolytes, particularly 0.9% NaCl, and polyols, such as mannitol, may be used to achieve the desired range.

It is a surprising discovery of the present invention that such comfort is enhanced when poloxamer at a concentration of about 3% or above is combined with a viscosity enhancer with no or reduced tonicity enhancement of about 25-150 mOsm/kg, and that poloxamer alone is highly irritating topically at a 3% or greater concentration.

Solubility

The solubility of α-2 agonists decreases exponentially at an increased pH. Table 2 illustrates the relationship between pH and solubility in water for dexmedetomidine. It shows that the soluble concentration of dexmedetomidine falls exponentially with higher pH. For pH of 4.0-6.0 a very high degree of solubility exists.

TABLE 2

| pH solution | solubility (mg/ml) | max soluble concentration |
| --- | --- | --- |
| 6.0 | 1.953 | 0.195% |
| 6.4 | ~0.60 | 0.060% |
| 7.0 | 0.224 | 0.023% |
| 7.4 | ~0.150 | 0.015% |
| 8.0 | 0.134 | 0.013% |

To achieve the greatest solubility while retaining the activity, the inventive compositions should include a salt; a poloxamer at a concentration of 12% weight by volume or less; and a viscosity enhancer. For example, using the provided compositions, dexmedetomidine is rendered soluble up to or beyond 0.15%.

Solubility for dexmedetomidine and other similar drugs in its subclass is typically reduced exponentially with increasing pH. For example, dexmedetomidine is only soluble in physiologic saline to about 0.025% at a highly alkaline pH. It is believed that the inventive formulations result in enhancement of solubility of dexmedetomidine, and by extension other members of its subclass, well above the 0.125% at alkaline pH.

It is believed the activity of the α-2 agonists, and dexmedetomidine in particular, in physiologic saline may be negatively affected by excipients of certain hydrophilicity or polarity, including citrate, various viscosity enhancing agents such as polyvinyl alcohol, various buffers such as phosphate buffer, and various gelling agents such as xanthan gum.

Thus, it is inventive and not trivial that only a very limited number of specific combinations of the ingredients lead to a greater activity and stability, and is therefore unexpectedly superior to other similar formulations. This result was not at all predictable and is not likely to be due to simply gelling or enhancing viscosity: for example, neither Xanthan gum, Carbopol 954, nor carboxymethylcellulose alone or in combination conferred the effectiveness equal to that of brimonidine.

It is therefore very unexpected and surprising that the ingredients of the provided formulations not only offer an improved efficacy compared to dexmedetomidine formulations in physiologic saline, but also make the formulations superior to brimonidine formulations. This is surprising because prior art comparisons of dexmedetomidine and brimonidine under similar conditions demonstrated brimonidine to be the preferred alpha 2 agonist. Such prior art testing demonstrated that dexmedetomidine (and clonidine) resulted in less IOP reduction with greater systemic absorption than brimonidine. It is therefore surprising and unexpected that under specific and very limited formulation conditions, dexmedetomidine is more effective than prior art formulations of dexmedetomidine and more effective than brimonidine by about 200% (IOP reduction vs. time, which is the key measure of the effectiveness of IOP reduction).

Other agents that improve solubility which may be used for the purposes of the present invention (as long as a salt, a poloxamer and a viscosity enhancers are included in the compositions) include, but are not limited to, polyanionic (multiple negatively charged) compounds, such as methylcellulose and derivatives, particularly carboxymethyl cellulose (CMC) or other cellulose derivatives; hypotonic saline; sodium acetate, calcium salt, methanesulfonate (mesylate), hydrobromide/bromide, acetate, fumarate, sulfate/bisulfate, succinate, citrate, phosphate, maleate, nitrate, tartrate, benzoate, carbonate, pamoate, borate, glycolate, pivylate, sodium citrate monohydrate, sodium citrate trihydrate, sodium carbonate, sodium ethylenediaminetetraacetic acid (EDTA), phosphoric acid, pentasodium pentetate, tetrasodium etidronate, tetrasodium pyrophosphate, diammonium ethylenediamine triacetate, hydroxyethyl-ethylenediamine triacetic acid, diethylenetriamine pentaacetic acid, nitriloacetic acid, and various other alkaline buffering salts, and/or addition of cyclodextrins and/or their derivatives, particularly (2-Hydroxypropyl)-beta-cyclodextrin; certain solvents such as Tween® 20, Tween® 80, polyvinyl alcohol, propylene glycol and analogues or derivatives thereof; certain osmotic agents, such as mannitol or sucrose, hydroxypropylmethylcellulose (HPMC) or analogues and/or derivatives thereof, or certain chelating agents.

In some preferred embodiments, the composition includes sodium citrate dehydrate at about 0.17%, and/or sodium acetate at about 0.39%; and/or calcium salt at about 0.048%.

Compositions and Methods of the Present Invention

Compositions and methods of the inventions encompass all isomeric forms of the described α-2 adrenergic receptor agonists, their racemic mixtures, enol forms, solvated and unsolvated forms, analogs, prodrugs, derivatives, including but not limited to esters and ethers, and pharmaceutically acceptable salts, including acid addition salts. Examples of suitable acids for salt formation are hydrochloric, sulfuric, phosphoric, acetic, citric, oxalic, malonic, salicylic, malic, fumaric, succinic, ascorbic, maleic, methanesulfonic, tartaric, and other mineral carboxylic acids well known to those in the art. The salts may be prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.,* 66: 1-19 (1977) which is incorporated herein by reference).

As long as a particular isomer, salt, analog, prodrug or other derivative of a suitable selective α-2 adrenergic receptor agonist functions as a suitable selective α-2 agonist, it may be used for the purposes of the present invention.

In some embodiments, compositions and methods of the invention include selective α-2 adrenergic receptor agonists which have binding affinities (K) for α-2 over α-1 receptors of 1000 fold or greater and are highly lipophilic, having an octanol-water partition coefficient of about 2.00 or greater. Brimonidine, by comparison, has a binding affinity for a-2 over a-1 receptors of about 976 and its lipophilicity range, even when optimized by pH, is about three hundred fold less than that of dexmedetomidine, a preferred embodiment.

In yet other embodiments, compositions and methods of the invention include selective α-2 adrenergic receptor agonists which have $K_i$ for α-2 over α-1 receptors of 1000 fold or greater and are at a concentration from between about 0.001% to about 0.035% weight by volume.

In some embodiments, compositions and methods of the invention include selective α-2 adrenergic receptor agonists which have K for α-2 over α-1 receptors of 1500 fold or greater, are present at a concentration from between about 0.010% to about 0.040% weight by volume, and have pH of about 6.2 or less.

In some embodiments, the compositions of the invention may also include other therapeutic agents; however, the compositions are intended to be effective without the need for any other therapeutic agents, specifically including, but not limited to, α-1 antagonists.

The invention also provides methods of treating and/or preventing glaucoma with the provided compositions. The provided methods lower IOP in glaucoma patients, reduce redness, and provide eye whitening. The provided methods may also treat ischemic optic neuropathy and other neuropathies of various etiologies due to neuroprotective effects of the provided compositions.

The compositions of the present invention are preferably formulated for a mammal, and more preferably, for a human. In one embodiment of the invention, the compositions are delivered as ophthalmic solutions into the eyes. The invention also contemplates topical compositions which include, but are not limited to, gels and creams. They may also include additional non-therapeutic components, which include, but are not limited to, preservatives, delivery vehicles, tonicity adjustors, buffers, pH adjustors, antioxidants, tenacity adjusting agents, mucoadhesive agents, viscosity adjusting agents, and water.

To make the topical compositions of the present invention, one can simply dilute more concentrated solutions of selective α-2 agonists, using methods known in the art with diluent of particular gelling agents in solution, being in a preferred embodiment Poloxamer 407, Poloxamer 188, or a combination thereof. In addition, the inventive formulations may optionally include one or more of electrolytes or tonicity enhancing agents, and preferably one or more of the weak acids and/or their salts to achieve a formulated pH of 4.0 to 8.0, and more preferably 5.5-6.5.

One preferred method of carrying out the dilutions involves overnight refrigeration, solubilizing both the active drug and the other excipients. This is a well known technique for solubilizing drugs for use with poloxamers. However, other methods can also be used. The compositions of the invention may include various inactive ingredients commonly used in formulating topical compositions and that may improve stability of the formulation. For example, the compositions of the invention may include alcohols and/or surface active agents, including but not limited to polyglycol ether, polyethylene glycol-nonphenol ether, polyethylene glycol sorbitan monolaurate, polyethylene glycol sorbitan monooleate, polyethylene glycol sorbitanmonooleate, polyethylene glycol sterarate, polyethylene glycol polypropylene glycol ether, polyvinyl alcohol, polyvinyl pyrrolidine, PEG and its derivatives, including but not limited to PEG 4000 or PEG 6000, in a total amount of 0.05% to 5% by mass of the composition.

In some embodiments, the compositions of the invention may include acids or monoglycerides of fatty acids having 8 to 12 carbon atoms, which when in 0.5-1.5 M, and preferably equimolar concentration to the alpha 2 agonist may improve corneal permeation via ion pair formation; or antioxidants such as ion-exchange/photooxidation stabilizing agents, including but not limited to citric acid, sorbic acid, boric acid, caprylic acid, glyceryl monocaprylate, glyceryl monocaproate, glycerol monolaurate, sodium metabisulfite.

In some embodiments, the compositions and methods of the present invention may include chelating agents that further improve stability, including but not limited to ethylenediaminetetraacetic acid (EDTA) and structurally related acids and even more preferably citric acid or its salt. In some embodiments, the chelating agents are present at a concentration of between 0.005% and 0.2% weight/vol.

Preservatives include, but are not limited to, benzalkonium chloride (BAK), methylparaben, polypropylparaben, chlorobutanol, thimerosal, phenylmercuric acetate, perborate, or phenylmercuric nitrate. BAK, in particular, has been found to be effective with preferred embodiments.

Delivery vehicles include, but are not limited to, polyvinyl alcohol, polyethyleneglycol (PEG) and its analogues, povidone, hydroxypropyl methyl cellulose, poloxamers, carboxymethyl cellulose (CMC), hydroxyethyl cellulose and purified water. It is also possible to use a physiological saline solution as a major vehicle.

Tonicity adjustors include, but are not limited to, a salt such as sodium chloride, potassium chloride, dextran, cyclodextrins, mannitol, dextrose, glycerin, or another pharmaceutically or ophthalmically acceptable tonicity adjustor. In some embodiments, the tonicity modifying agents are present at a concentration of between 0.1% and 1% weight by volume.

The compositions of the present invention may comprise corneal permeation enhancing agents which include, but are not limited to, preservatives, cyclodextrins, viscosity enhancers, and ion-channel enhancing agents. In some embodiments, corneal permeation enhancing agents include citrate, a citrate salt and/or other salts which increase solubility, chelating agents such as EDTA, preservatives, ion-channeling agents, cyclodextrin, or other additives which increase corneal permeability.

In some embodiments of the invention, a corneal permeation enhancing agent may be selected from the group consisting of BAK at 0.01% to 0.02% weight by volume, EDTA at 0.005% weight by volume, caprylic acid, citric acid, boric acid, sorbic acid and/or salts, derivatives, and analogues thereof, where citric acid or its salt is a preferred embodiment.

In some embodiments, the compositions and methods of the present invention may include additional viscosity enhancers and/or agents increasing solubility and/or stability, including but not limited to polyvinylpyrrolidone, polyethylene glycol (PEG), cellulose or cellulose derivatives of various molecular weights, including methylcellulose, cellulose glycolate, hydroxypropylcellulose, CMC and its salts, gelatin, sorbitol, alpha-cyclodextrin and/or other cyclodextrin derivatives, niacinamide, carbomers of various molecular weights including carbomer 934 P and 974 P, xanthan gums, alginic acid, guar gums, locust bean gum, chitosan, propylene glycol, polyvinyl alcohol, polysorbate including polysorbate 80, glycerin, mannitol, benzyl alcohol, phenylethyl alcohol, povidone, borate, acetate, phosphate or other similar buffering salts or agents, BAK, methyl paraben, sodium bisulfite, or peroxide preservative systems, surfactants, etc. In some embodiments, these agents are present at a total amount of 0.05% to 5% by w/v.

Many of the listed additives (for example, BAK, EDTA, etc) may serve more than one purpose: for example, they can serve as both preservatives and corneal permeation enhancing agents (e.g. BAK), or solubilizing, preservative, and corneal permeation enhancing agents (e.g. citrate).

Buffers and pH adjustors include, but are not limited to, acetate buffers, carbonate buffers, citrate buffers, phosphate buffers and borate buffers. It is understood that various acids or bases can be used to adjust the pH of the composition as needed. pH adjusting agents include, but are not limited to, sodium hydroxide and hydrochloric acid. Antioxidants include, but are not limited to, sodium metabisulfite, sodium thiosulfate, acetylcysteine, butylated hydroxyanisole and butylated hydroxytoluene.

Use of Provided Formulations as Vehicles for Drug Delivery

Dryness is a common problem with topical use of alpha 2 agonists for glaucoma as well as many other topical eye medications. For example, more than 10% of brimonidine users complain of dryness. The formulations of the present invention were tested as a vehicle without the active agent (dexmedetomidine) after substantial wetting and comfort was observed with its use.

Thus, in one embodiment, the invention provides a vehicle formulation for drug delivery, wherein said vehicle formulation comprises a poloxamer, hypotonic saline, and a viscosity enhancer, at the same concentrations and ranges as previously recited.

The provided vehicle formulations may intraocularaly deliver dexmedetomidine and other drugs, particularly lipophilic drugs, with improved efficacy and reduced systemic absorption. The drugs which can be delivered with vehicle formulations of the present invention include Ketoralac® and other non-steroidal agents, prednisone and other steroidal agents, latanaprost and other prostaglandins, prostanoids and other prostaglandin analogues, α-1 antagonists such as phentolamine, anti-viral drugs, anti-microbial drugs, anti-fungal drugs, anti-VEGF drugs, and/or other drugs.

These vehicle formulations dramatically enhanced the comfort and wetting effect after application. Wetting was appreciably improved with extended tear breakup times for up to about 55 minutes after application, and with initial blurring of vision resolving after only about 15-40 seconds. These effects allowed for a more prolonged duration in which eyes could be kept open for several seconds longer between blinks (up until about 55 minutes after instillation (a measure of improved tear "wetability" of the cornea. In contrast, the longest duration artificial tear gels currently available, such as Celluvisc®, which provides similar improved tear breakup time up to about 60 minutes after instillaiton, causes significant blurring for about 5 to 10 minutes after instillation, reducing the effectiveness of prior art formulations vs. the vehicle of the present invention as both an artificial tear and as a possible vehicle for ophthalmic drug delivery.

Thus, in one embodiment, the invention provides an artificial tear solution comprising:
  i. a hypotonic salt or sterile water;
  ii. a poloxamer at a concentration of 12% weight by volume or less;
  iii. a viscosity enhancer, and
  wherein said pharmaceutical solution has a viscosity of between 25 and 500 cps.

The following Examples are provided solely for illustrative purposes and are not meant to limit the invention in any way.

Example 1

Intraocular Pressure (IOP), Redness and Burning/Stinging

Experimental Design

Various formulations of α-2 agonists were unilaterally administered to a normotensive (<21 mm Hg) human subject. The subject first underwent baseline IOP testing using standard applanation tonometry via slit lamp. After fluorescein instillation, the drug was instilled as a morning dose at between about 7:00 and 9:00 AM. Preliminary measurements at 2, 3, 3.5, 4 and 4.5 hours demonstrated a substantial peak effect between about 3.45 and 4.15 hours for a preferred formulation of the invention. Follow up IOP checks were designed to be about 4 hours after initial instillation, where instillation consisted of 1-2 drops.

Experimental Results

The comparative human studies of: a) a preferred embodiment of the present invention versus; b) a dexmedetomidine formulation without poloxamer; and c) brimonidine demonstrate significant therapeutic advantages of the inventive composition over prior art.

In particular, testing of prior art formulations of dexmedetomidine (in phosphate buffer 6.4) and brimonidine (Alphagan P®) were consistent with published data showing 30-35% IOP reduction in normotensive rabbits (equivalent to about 20% reduction in normotensive human eyes which have thicker corneas and less intraocular penetration). In contrast, the present invention demonstrates a surprising increase in IOP reduction, peaking at about 4 hours (versus, 2 hours for brimonidine), nearly two-fold greater IOP reduction versus brimonidine, greater topical comfort, greater redness reduction, reduced topical side effects, and reduced systemic side effects.

Table 3 demonstrates the results of this experiment.

TABLE 3

| Drug | IOP Reduction @ 4 hrs post instillation | Induced Redness | Burning - Stinging on instillation |
|---|---|---|---|
| Brimonidine 0.20% (prior art formulation) | 20% | 25% incidence | >10% incidence |
| Dexmedetomidine 0.10% in phosphate buffer pH 6.4; BAK 0.02% (Prior art formulation) | 20% | Whitens | None |
| Dexmedetomidine 0.10% in poloxamer gel 5-6%; CMC high blend 0.72%; 0.25% saline; BAK 0.02%, pH 5.5-6.0 (Preferred embodiment) | 40% | Whitens | None, prolonged lubricating action of about 55 minutes |

Tables 4-8 summarize studies of various formulations and excipients with dexmedetomidine. In particular, Table 4 demonstrates that there are significant side effects, such as sedation, when dexmedetomidine concentration is at or greater than about 0.02%, Table 5 demonstrates substantial and surprising improvements over Table 4 and prior art studies with the preferred embodiment of dexmedetomidine.

TABLE 4

Poloxamer, Normal Saline

| | Formulations | | | | | | |
|---|---|---|---|---|---|---|---|
| | 1 | 2 | 3 | 4 | 5 | 6 | 7 |
| Components | | | | | | | |
| Dexmedetomidine | 0.02% | 0.02% | 0.05% | 0.05% | 0.05% | 0.05% | 0.07% |
| CMC high viscosity blend | — | — | — | — | — | — | — |
| NaCl | 0.90% | 0.90% | 0.90% | 0.90% | 0.90% | 0.90% | 0.90% |
| Poloxamer 407 | — | — | — | — | 2-3% | — | — |
| Poloxamer 407 * | — | — | — | — | — | 2-3% | — |
| Xanthan Gum | — | — | — | — | — | — | — |
| BAK | 0.01% | 0.01% | 0.01% | 0.01% | 0.01% | 0.01% | 0.01% |
| EDTA | — | — | — | — | — | — | — |
| PVA | — | — | — | — | — | — | — |
| PVP | — | — | — | — | — | — | — |
| citric acid | — | — | — | — | — | — | — |
| pH | 7 | 4.5-5.2 | 4.5-5.2 | 7.0-7.5 | 4.5-5.5 | 4.5-5.5 | 4.5-5.5 |
| Effects | | | | | | | |
| Peak IOP reduction | 18% | 20% | 22% | 20% | 20-22% | 20-22% | 25% |
| Side effects (0-4) | | | | | | | |
| Bradycardia | 0 | 0 | 1 | 1 | 1 | 1 | 2.5 |
| Stinging | 0 | 1 | 1 | 1 | 1 | 1 | 1 |
| Dry Mouth | 0 | 0 | 2 | 2 | 2 | 2 | 2.5 |
| Sedation | 0 | 0.5 | 1.5 | 1.5 | 1.5 | 1.5 | 2 |
| Rate ("−" bad, "+++++" best) | − | + | − | −− | −− | −− | −− |

* different source

TABLE 5

CMC, Poloxamer, Normal Saline

| | Formulations | | | | | | |
|---|---|---|---|---|---|---|---|
| | 8 | 9 | 10 | 11 | 12 | 13 | 14 |
| Components | | | | | | | |
| Dexmedetomidine | 0.07% | 0.07% | 0.07% | 0.07% | 0.07% | 0.07% | 0.07% |
| CMC high viscosity blend | 0.50% | 0.92% | 0.62% | | 0.92% | 0.62% | 0.62% |
| NaCl | 0.90% | 0.90% | 0.90% | 0.90% | 0.90% | 0.90% | 0.25% |
| Poloxamer 407 | — | — | — | — | — | — | — |
| Poloxamer 407 * | — | — | — | 2-3% | 2-3% | 2-3% | 2-3% |
| Xanthan Gum | — | — | — | — | — | — | — |
| BAK | 0.01% | 0.01% | 0.02% | 0.02% | 0.02% | 0.02% | 0.02% |
| EDTA | — | — | — | — | — | — | — |
| PVA | — | — | — | — | — | — | — |
| PVP | — | — | — | — | — | — | — |
| citric acid | — | — | — | — | — | — | — |
| pH | 4.5-5.5 | 4.5-5.5 | 4.5-5.5 | 4.5-5.5 | 4.5-5.5 | 4.5-5.5 | 4.5-5.5 |
| Effects | | | | | | | |
| Peak IOP reduction | 20-22% | 20-25% | 25-30% | 25-30% | 25-30% | 25-30% | 25-30% |
| Side effects (0-4) | | | | | | | |
| Bradycardia | 1 | 0 | 0 | 2 | 0 | 0 | 0 |
| Stinging | 1 | 1 | 1 | 1 | 1 | 1 | 1 |
| Dry Mouth | 2 | 0 | 1 | 1 | 0 | 1 | 1 |
| Sedation | 1 | 0 | 0 | 0 | 0 | 0 | 0 |
| Rate ("−" bad, "+++++" best) | + | + | + | ++ | + | ++ | +++ |

* phosphate buffered

TABLE 6

Poloxamer, CMC, Hypotonic NaCl, pH

| | Formulations | | | | | | | |
|---|---|---|---|---|---|---|---|---|
| | 15 | 16 | 16A | 16b | 16b2 | 17 | 18 | 19 |
| Components | | | | | | | | |
| Dexmedetomidine | 0.075% | 0.07% | 0.085% | 0.100% | 0.100% | 0.07% | 0.07% | 0.07% |
| CMC high viscosity blend | — | 0.62% | 0.62% | 0.62% | 0.75% | 0.62% | 0.62% | 0.62% |
| NaCl | 0.90% | ≦0.25% | ≦0.25% | ≦0.25% | ≦0.25% | ≦0.25% | ≦0.25% | ≦0.25% |
| Poloxamer 407 | — | — | — | — | — | — | — | — |
| Poloxamer 407 * | 5% | 5-6% | 5-6% | 5-6% | 5-6% | 5-6% | 5-6% | 5-6% |
| Xanthan Gum | — | — | — | — | — | — | — | — |
| BAK | 0.02% | 0.02% | 0.02% | 0.02% | 0.02% | 0.02% | 0.02% | 0.02% |
| EDTA | — | — | — | — | — | — | — | — |
| PVA | — | — | — | — | — | 0.30% | — | 0.30% |
| PVP | — | — | — | — | — | — | 0.30% | 0.30% |
| citric acid | — | — | — | — | — | — | — | — |
| pH | 4.5-5.5 | 4.5 | 4.5 | 4.5 | 5.5-7.0 | 4.5-5.5 | 4.5-5.5 | 4.5-5.5 |
| Effects | | | | | | | | |
| Peak IOP reduction | 30% | 40% | 40% | 40% | 40% | 40% | 35% | 35% |
| Side effects (0-4) | | | | | | | | |
| Bradycardia | 0 | 0 | 0 | 0.5 | 0.5 | 0 | 0 | 0 |
| Stinging | 2 | 0.5 | 0.5 | 0.5 | 0 | 0.5 | 0.5 | 0.5 |
| Dry Mouth | 1.5 | 0.5 | 0.5 | 0.5 | 0.5 | 0.5 | 0.5 | 0.5 |
| Sedation | 0 | 0 | 0 | 1 | 0-1 * | 0 | 0 | 0 |
| "+++++" best) | +++½ | +++½ | +++½ | ++++ | ++++½ | +++ | +++ | +++ |

* alternate source
** 0 with 30 sec punctal occlusion

TABLE 7

Other Viscosity Enhancers, Xanthan Gums, Poloxamer, pH

| | Formulations | | | | |
|---|---|---|---|---|---|
| | 20 | 21 | 22 | 23 | 24 |
| Components | | | | | |
| Dexmedetomidine | 0.07% | 0.075% | 0.075% | 0.075% | 0.075% |
| CMC high viscosity blend | — | — | — | — | — |
| NaCl | ≦0.25% | 0.50% | 0.50% | 0.50% | 0.50% |
| Poloxamer 407 | — | — | — | — | — |
| Poloxamer 407* | 5-6% | — | — | — | — |
| Xanthan Gum | — | 0.100% | 0.100% | 0.120% | 0.120% |
| BAK | 0.01% | 0.01% | 0.01% | 0.01% | 0.01% |
| EDTA | 0.01% | — | — | 0.01% | 0.01% |
| PVA | 0.30% | — | — | — | — |
| PVP | 0.30% | — | — | — | — |
| citric acid | 0.03% | — | — | — | — |
| pH | 7.0-7.5 | 4.5 | 5.2 | 4.5 | 5.2 |
| Effects | | | | | |
| IOP ↓, peak | 20-25% | 15% | 20% | 25% | 25% |
| Side effects (0-4) | | | | | |
| Bradycardia | 1 | 1 | 1 | 1 | 1 |
| Stinging | 0-1 | 0-1 | 0-1 | 0-1 | 0-1 |
| Dry Mouth | 1.5x | 0 | 0 | 0 | 0 |
| Sedation | | | | | |
| Rate ("—" bad, "+++++" best) | +½ | ½ | ½ | ½ | ½ |

*phosphate buffered

TABLE 8

Xanthan Gums, NaCl, Polysorbate 80

| | Formulations | | | | | | | |
|---|---|---|---|---|---|---|---|---|
| | 25 | 26 | 27 | 28 | 29 | 30 | 31 | 32 |
| Components | | | | | | | | |
| Dexmedetomidine | 0.100% | 0.100% | 0.120% | 0.120% | 0.120% | 0.120% | 0.150% | 0.150% |
| Xanthan Gum ** | 0.075% | 0.075% | 0.085% | 0.085% | 0.100% | 0.100% | 0.100% | 0.100% |
| NaCl | 0.250% | 0.250% | 0.250% | 0.250% | 0.250% | 0.250% | 0.250% | 0.250% |
| Polysorbate 80 | 0.050% | 0.050% | 0.050% | 0.050% | 0.050% | 0.050% | 0.050% | 0.050% |
| BAK | 0.010% | 0.010% | 0.010% | 0.010% | 0.010% | 0.010% | 0.010% | 0.010% |
| mannitol | — | — | — | — | — | — | — | — |
| EDTA | — | — | — | — | 0.01% | 0.01% | 0.01% | 0.01% |
| citric acid | — | — | — | — | — | — | — | — |
| pH | 5.2 | 4.5 | 5.2 | 4.5 | 5.2 | 4.5 | 4.5 | 4.5 |

TABLE 8-continued

Xanthan Gums, NaCl, Polysorbate 80

| | Formulations | | | | | | | |
|---|---|---|---|---|---|---|---|---|
| | 25 | 26 | 27 | 28 | 29 | 30 | 31 | 32 |
| Effects | | | | | | | | |
| IOP Reduction | 20% | 18% | 25% | 22% | 28% | 25% | 25% | 25% |
| Sedation | 2.00 | 2.00 | 2.50 | 2.50 | 2.75 | 2.75 | 2.75 | 2.75 |
| Rate ("−" bad, "+++++" best) | + | + | + | + | + | + | + | + |

As Tables 4-8 demonstrate, the most effective compositions with lowest side effect profile are those which contain poloxamer at about 5-6%, CMC, sodium chloride and BAK. The peak dose response IOP reduction for preferred embodiments of the present invention appeared to be between about 0.070%-0.10%.

Example 3

Effect of Topical Administration of Dexmedetomidine at on Cosmetic Appearance of the Eyes Experimental Design The purpose of this experiment was to evaluate effect of dexmedetomidine on cosmetic appearance (i.e., whiteness) of the treated eyes at concentrations of 0.010%; 0.022%: 0.050%; and 0.10% within a pH range of 4.5-6.0. The tested dexmedetomidine solution contained poloxamer at 6%; NaCl at 0.25%; CMC high blend at 0.50-0.75%; and BAK at 0.02%. The experiment was designed as follows:

1-2 drops of dexmedetomidine were topically applied to one eye of an individual. Eye whiteness prior to and after the application was visually measured by the patient on a scale of 0 (white eye, no hyperemia) to 4 (significantly reddened eye, strong hyperemia), with measurements taken at about 30 min to 3 hours after instillation.

Experimental Results

TABLE 9

| Dexmedetomidine Concentration | Redness | Eye White Shade |
|---|---|---|
| Baseline | 1.5 | 1 |
| 0.010% | 1.25 | 1 |
| 0.022% | 1.25 | 1.25 |
| 0.050% | 1.0 | 1.5 |
| 0.075% | 1.0 | 1.5 |
| 0.10% | 0.75 | 1.75 |

*Poloxamer 6%; NaCl 0.25; CMC Hi blend 0.50-0.75%; BAK 0.02%
Conventional Redness Scale: 0 (none)-4 (reddest + chemosis),
Eye White Shade: 4 (whitest)-1 off-white-gray/yellow The decrease in hyperemia and increase in whiteness started about 2 minutes after the application. The maximum whiteness was reached in about 10 minutes, with a gradual and slow decline over a period of several hours thereafter. The total duration of the effect both in terms of reduced hyperemia and increase in whiteness was about 3-5 hours. Although the effect both in terms of decreased redness and whitening was modest, it was nevertheless noticeable and cosmetically beneficial to the subject, particularly at dexmedetomidine concentrations of 0.050% and above.

The experiment has demonstrated that dexmedetomidine at 0.010% provides noticeable hyperemia reduction and 0.050% and above effects modest but noticeable cosmetic improvement via eye whitening.

Example 4

Effects on Intraocular Pressure (IOP) and Side Effects

Experimental Design

First, baseline IOP measurements were performed on a subject using applanation slit lamp tonometry following instillation of fluorescein. Then, two drops of the topical agent to be tested were applied seconds apart to the left eye, and the punctum occluded for 30 seconds. Approximately four hours later, IOP testing was again performed. Three initial readings were taken and discarded to ensure minimal patient blepharospasm, following which the next three readings were recorded and averaged. There was a washout period of several days—1 week between tests. All baseline IOP measurements were between 15.0-15.5 mm Hg at 8:00 AM-9:00 AM at the time of instillation.

Side effects were qualitatively graded from 0-4 (0—no side effects; 4—high degree of side effects (stinging on instillation, eye dryness, pharyngeal dryness, fatigue, sedation)) for the two tested dexmedetomidine formulations.

Experimental Results

The comparative human studies of: a) a preferred embodiment of the present invention versus; b) a dexmedetomidine formulation at 0.10% in a buffered phosphate at pH 6.4-6.5 without poloxamer; and c) brimonidine, demonstrated significant therapeutic advantages of the inventive composition over prior art formulations of brimonidine or dexmedetomidine.

The present invention demonstrates a surprising increase in IOP reduction, nearly two-fold greater IOP reduction versus brimonidine, greater topical comfort, greater redness reduction, reduced topical side effects, and reduced systemic side effects.

Table 10 demonstrates the results of this experiment.

TABLE 10

| Drug | IOP # | IOP %↓ | Pharynx Dryness | Stinging | Redness | Eye Dryness | Comfort | Sedation |
|---|---|---|---|---|---|---|---|---|
| Alphagan ® | 11.7 | 23.3% | 10-30%* | 10-30%* | 10-30%* | 3-9%* | 2 of 4 | 10-30%* |
| Dexmedetomidine 0.10% w phosphate buffer | 12.0 | 21.4% | 2 of 4 | 0 of 4 | 0 of 4 | 0 of 4 | 3 of 4 | 2 of 4 |
| Preferred Embodiment** | 9.2 | 39.6% | 0.5 of 4 | 0 of 4 | 0 of 4 | 0 of 4 | 4 of 4 | 0 of 4 |

*Published data
**Dexmedetomidine 0.10%, Poloxamer gel 5-6%. CMC high blend 0.75%. BAK 0.02%, pH 6.0

This experiment demonstrated that the provided inventive compositions result in a substantially greater therapeutic benefit than prior art formulations of brimonidine or dexmedetomidine with improved systemic and topical side effect profile.

Example 5

Effect of Carbopol® 954 and Poloxamer 407 on Dexmedetomidine, with and without Viscosity Agent Enhancement, with and without NaCl Experimental Design The goal of this experiment was to investigate the effects of adding Carbopol® 954 (C) and Poloxamer 407 (P) (both separately and in combination) on the effectiveness of topical dexmedetomidine at 0.025% weight by volume in normal saline. The concentrations of Carbopol® 954P and Poloxamer 407 ranged from 1% to 8%.

Experimental Results

Table 11 demonstrates the results of this experiment.

TABLE 11

| Formulation | pH | Stinging 0-4 | Color | IOP Effect | Observation |
|---|---|---|---|---|---|
| C1% | 4.5-6.5 | 1-2+ | Turbid | <= prior art | Cloudy solution |
| C2%-5% | 4.5-6.5 | | | | Too thick at all pH levels tested |
| P1-2% | 4.5-6.5 | 1+ | Clear | <= prior art | |
| P4%-6% | 4.5-6.5 | 2+ | Clear | Not tested | Hi pharyngeal dryness, sedation risk |
| P8% | 4.5-6.5 | 4+ | Clear | Not tested | Poorly tolerated |
| P2% + C 1% | 4.5-6.5 | 1.5+ | Turbid | Not tested | Uncomfortable |
| P1-10% + high blend CMC 0.25% | 4.5-6.5 | 1+ | Clear | ≧25% | Moderately uncomfortable. Mod-hi pharyngeal dryness |
| P1-10% + high blend CMC 0.50-0.75% + Nacl 0.025% | 4.5-7.0 | 0-0.25 (slight, transient <=15 seconds) | Clear | ≧30% with high of 40% at 5-6% no pH effect | Great comfort, barely noticeable pharyngeal dryness |
| P1-10% + high blend CMC 0.50-0.75% + Nacl 0.025% w/o dexmedetomidine | 6.5 | 0-0.25 (slight, transient <=15 seconds) | Clear | Not tested | Tear break up time improvement 30-55 minutes; initial blurring 30-60 seconds. |

C: Carbomer 934P
P: Poloxamer 407

As Table 14 demonstrates, neither Poloxamer 407 alone nor Carbomer 934P alone provided satisfactory topical comfort for human use. However, a combination of specific concentrations of Poloxamer 407 and a viscosity agent (such as CMC) provided improved comfort and IOP reduction. There was an additional comfort and even stronger IOP reduction effect at more hypotonic solutions.

In particular, a combination of Poloxamer 1-10%, a viscosity agent and reduced salinity provided excellent comfort. The best formulation contained Poloxamer 5-6%+high blend CMC 0.62-0.75%+NaCl 0.025%. It provided best comfort, IOP effect treated eye and least local-systemic effect (pharyngeal dryness).

Example 6

Comparison of Treated and Non-Treated Eye Intraocular Pressure with Brimonidine 0.20%, Dexmedetomidine 0.010% in Phosphate Buffered Saline Vs. Dexmedetomidine Preferred Embodiment*

Experimental Design

The following formulations were compared:
a) brimonidine (Alphagan® P) (Composition B)
b) dexmedetomidine at 0.01%, phosphate buffered to pH 6.4 (Composition C); and
c) dexmedetomidine at 0.1% with 5% Poloxamer 407 (F127), 0.25% NaCl, CMC high blend 0.75%, and BAK 0.02% at pH 6.1 (Composition A) (preferred embodiment).

Two drops of each of the tested formulations were placed in the left eye of a subject without punctual occlusion on separate days with a washout (break) (between several days to a week) between the administrations. Intraocular pressure measurements were taken 2.5 and 3.75 hours later in both the treated and non-treated eye.

Experimental Results

Table 12 demonstrates the results of this experiment.

AM, followed by 30 seconds of punctual occlusion with application on days 1, 3, and 5.

IOP was measured at one or more of 4 hrs, 8 hrs, 12 hrs, 24 hrs, 32 hrs and comfort and side effect profile were qualitatively assessed.

TABLE 12

| Drug | IOP Baseline (Treated Eye) mm Hg | IOP 2.5 hours (Treated Eye) mm Hg | IOP 4 hours (Treated Eye) mm Hg | IOP Baseline (Non-Treated Eye) mm Hg | IOP 2.5 Hours (Non-Treated Eye) mm Hg | IOP 4 Hours (Non-Treated Eye) mm Hg | % Non Treated Eye to Treated Eye (IOP Max Reduction) mm Hg |
|---|---|---|---|---|---|---|---|
| Composition A | 15 | 10 (33% reduction) | 9.3 (40% reduction) | 15.5 | 14 (6.6% reduction) | 14 (6.6% reduction) | 16.5% |
| Composition B | 15 | 12 (20% reduction) | 12.5 (16.6% reduction) | 15 | 14 (6.6% reduction) | 14 (6.6% reduction) | 33% |
| Composition C | 15 | 12 (20% reduction) | 12 (20% reduction) | 15 | 12.5 (16.6% reduction) | 13 (13.4% reduction) | 83% |

As Table 12 demonstrates, this experiment showed the following:

1) two-fold greater IOP peak % reduction in the treated eye with the inventive formulation (Composition A) vs. brimonidine (Composition B);

2) two-fold less IOP % reduction in the non-treated eye with the inventive formulation (Composition A) vs. brimonidine (Composition B);

3) two-fold greater IOP reduction in the treated eye after 4 hours with the inventive formulation (Composition A) vs. alternative dexmedetomidine formulation (Composition C); and 4) Longer duration of action to peak IOP reduction for the inventive formulation (Composition A) increasing from 2.5 hours to 4 hours vs. brimonidine (Composition B).

These results demonstrate improved efficacy and systemic absorption reduction of the inventive compositions as compared with similar dexmedetomidine compositions and conventional brimonidine compositions.

A greater differential of IOP reduction between treated and non-treated eye using the inventive compositions represents a lower systemic side effect profile as it is interpreted to correlate with reduced systemic absorption of drug reaching the non-treated eye.

Example 7

Effect of Composition a on IOP Vs. Baseline Over a 24 Hour Period

Experimental Design

Three subjects with normo-tensive baseline IOP (<21 mm Hg) were treated with a single instillation of two drops of the composition A (as described in Example 6) per eye at 8:30

Experimental Results

Table 13 demonstrates the results of this experiment.

TABLE 13

| Day | Time | right eye IOP mmHg mean | Reduction in % IOP | left eye | Reduction in % IOP |
|---|---|---|---|---|---|
| PATIENT NO. 1 | | | | | |
| 1 | 8 am | 17 | Baseline | 17 | Baseline |
|  | 10 am | 15 | 11.8% | 15 | 11.8% |
|  | 12 pm | 7 | 58.8% | 8 | 52.9% |
|  | 4 pm | 7 | 58.8% | 8 | 52.9% |
| 2 | 8 am | 12 | 29.4% | 12 | 29.4% |
|  | 4 pm | 15 | 11.8% | 16 | 5.9% |
| 5 | 8 am | 15 | Baseline | 16 | Baseline |
|  | 4 pm | 9 | 40.0% | 9 | 43.8% |
| PATIENT NO. 2 | | | | | |
| 1 | 8 am | 14 | Baseline | 12 | Baseline |
|  | 10 am | 11 | 21.4% | 10 | 16.7% |
|  | 12 pm | 9 | 35.7% | 9 | 25.0% |
|  | 4 pm | 8 | 42.9% | 9 | 25.0% |
| 2 | 8 am | 9 | 35.7% | 10 | 16.7% |
|  | 4 pm | 13 | 7.1% | 13 | N/A |
| 5 | 8 am | 16 | Baseline | 16 | Baseline |
|  | 4 pm | 11 |  | 12 |  |
| PATIENT NO. 3 | | | | | |
| 1 | 8 am | 12 | Baseline | 12 | Baseline |
|  | 10 am | 10 | 16.7% | 10 | 16.7% |
|  | 12 pm |  | N/A |  | N/A |
|  | 4 pm | 7 | 41.7% | 8 | 33.3% |
| 2 | 8 am | 12 | 0% | 12 | 0% |
|  | 4 pm | 12 | 0% | 11 | 8.3% |
| 5 | 8 am | 11 | Baseline | 11 | Baseline |
|  | 4 pm | 7 | 36.4% | 8 | 27.3% |

As Table 13 demonstrates, the tested inventive formulation achieved a peak IOP reduction effect at about 4 to 8 hours after instillation. Furthermore, in two out of three patients the IOP remained below the baseline 24 hours after instillation. Typically, conventional brimonidine formulations achieve a peak IOP reduction effect of only about 15-18% in normo-tensive eyes about 2-3 hours after instillation. The IOP reduc tion effect of the inventive formulation was much stronger: from 41.7% to 58.8% at 8 hours after instillation.

Therefore, the formulations of the invention demonstrate improved performance over brimonidine as well as other known glaucoma drugs under similar conditions of testing (1-2 days of use, normotensive eyes).

No significant local or systemic side effects were observed.

What is claimed is:

1. A pharmaceutical composition comprising
   i. dexmedetomidine as the only active ingredient at a concentration from between about 0.0125% to about 0.125% weight by volume;
   ii. a hypotonic salt or sterile water;
   iii. a poloxamer at a concentration of between 2% and 12% weight by volume;
   iv. a viscosity enhancer,
      wherein said pharmaceutical composition has a viscosity of between 25 and 500 cps, and
      wherein said pharmaceutical composition is effective for the treatment of glaucoma in a patient in need thereof.

2. The pharmaceutical composition of claim 1, wherein said dexmedetomidine is at a concentration from between about 0.035% to 0.10% weight by volume.

3. The pharmaceutical composition of claim 1, wherein said salt selected from the group consisting of sodium chloride, citrate, mesylate, hydrobromide/bromide, acetate, fumarate, sulfate/bisulfate, succinate, phosphate, maleate, nitrate, tartrate, benzoate, carbonate, and pamoate.

4. The pharmaceutical composition of claim 3, wherein said salt is sodium chloride.

5. The pharmaceutical composition of claim 1, wherein said viscosity enhancer is selected from carboxymethyl cellulose, methylcellulose, hydroxymethyl cellulose, hydroxypropylmethyl cellulose, hydroxyethyl cellulose, polyethylene glycol, dextran, povidone, alginic acid, guar gum, acacia, veegum, gelatin, chitosan, carbopol, locust bean gum, acidic polycarbophil, dextran, pectin, povidone, polyvinylpyrridone, polyvinyl alcohol, and hyaluronic acid.

6. The pharmaceutical composition of claim 5, wherein said viscosity enhancer is carboxymethyl cellulose.

7. The composition of claim 6, wherein said carboxymethyl cellulose is of a high blend at a concentration of between 0.1% and 1.25%.

8. The pharmaceutical composition of claim 1, wherein said poloxamer is present at concentration range of 5% to 6% by weight.

9. The pharmaceutical composition of claim 1, wherein said poloxamer is selected from the group consisting of poloxamer 407, poloxamer 188, and combinations thereof.

10. The pharmaceutical composition of claim 1, further comprising a buffer.

11. The pharmaceutical composition of claim 10, wherein said buffer is selected from the group consisting of citrate buffer, borate buffer, maleate buffer, succinate buffer, phosphate buffer, acetate buffer, sorbate buffer and carbonate buffer.

12. The pharmaceutical composition of claim 11, wherein said buffer is at a concentration between 4 mM and 10 mM.

13. The pharmaceutical composition of claim 1, further comprising a mucoadhesive.

14. A pharmaceutical composition comprising:
   i. dexmedetomidine as the only active ingredient at a concentration from between 0.02% and about 0.12% weight by volume;
   ii. sodium chloride at a concentration of 0.25% to 0.50%;
   iii. a poloxamer at a concentration of between 3% and 12% weight by volume;
   iv. carboxymethyl cellulose (CMC), and
   wherein said pharmaceutical composition has a viscosity of between 50 and 200 cps, and
   wherein said pharmaceutical composition is effective for the treatment of glaucoma in a patient in need thereof.

15. A method of treating glaucoma in a patient in need thereof comprising administering to said patient the pharmaceutical composition of claim 1.

* * * * *